(12) United States Patent
MacDonald et al.

(10) Patent No.: US 7,837,663 B2
(45) Date of Patent: *Nov. 23, 2010

(54) ODOR CONTROLLING ARTICLE INCLUDING A VISUAL INDICATING DEVICE FOR MONITORING ODOR ABSORPTION

(75) Inventors: John Gavin MacDonald, Decatur, GA (US); RameshBabu Boga, Roswell, GA (US); Jaeho Kim, Roswell, GA (US); Bao Trong Do, Decatur, GA (US); Irene Kuznetsov, Lawrenceville, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 940 days.

This patent is subject to a terminal disclaimer.

(21) Appl. No.: 10/687,269

(22) Filed: Oct. 16, 2003

(65) Prior Publication Data

US 2005/0112085 A1 May 26, 2005

(51) Int. Cl.
| | |
|---|---|
| *A61F 13/15* | (2006.01) |
| *A61F 13/47* | (2006.01) |
| *A61F 13/472* | (2006.01) |
| *A61F 13/49* | (2006.01) |
| *A62B 18/02* | (2006.01) |
| *A61K 8/00* | (2006.01) |
| *A61K 9/14* | (2006.01) |
| *A61K 33/00* | (2006.01) |
| *A61K 33/34* | (2006.01) |
| *A61K 9/70* | (2006.01) |

(52) U.S. Cl. .......... 604/387; 424/65; 424/443; 424/489; 424/600; 424/630; 424/646; 424/649; 604/358; 604/393; 604/400; 604/904; 977/707; 128/206.21

(58) Field of Classification Search .......... 424/76.1, 424/489, 641, 630, 646, 649, 724, 600, 443, 424/65; 128/206.21; 604/387, 358, 393, 604/400, 904; 977/707

See application file for complete search history.

(56) References Cited

U.S. PATENT DOCUMENTS 2,015,864 A 10/1935 Müller et al.

(Continued)

FOREIGN PATENT DOCUMENTS

EP 0103214 3/1984

(Continued)

OTHER PUBLICATIONS http://www.aapspharmaceutica.com/meetings/pastmeetings/particlesize/mitchell.pdf.*

(Continued)

*Primary Examiner*—Johann R Richter
*Assistant Examiner*—James H Alstrum Acevedo
(74) *Attorney, Agent, or Firm*—Dority & Manning, P.A.

(57) ABSTRACT

The present invention relates to a visual indicating device and an article for controlling odors, in particular foot, garbage, basement, cooking, pet, tobacco, feces and urine odors. The article comprises a visual indicating agent that is color sensitive to the odor, and optionally, an odor absorbing agent. The visual indicating agent changes color when the article has been exposed to a sufficient amount of odor to saturate the article. The indicating agent may be applied in differing concentrations to two or more zones so as to indicate to a user of the article how much of the odor absorbing capacity has been used, or conversely, how much of the odor absorbing capacity remains. Suitable visual indicating agents that change color in response to odors are also described. The article for controlling odors may be a disposable odor absorbing sheet, air freshening product, diaper, undergarment pad, face mask, air filtration device, sanitary napkin, tampon, panty shield or incontinence pad.

34 Claims, 3 Drawing Sheets

U.S. PATENT DOCUMENTS

| | | |
|---|---|---|
| 2,593,146 A | 4/1952 | Howard |
| 3,266,973 A | 8/1966 | Crowley |
| 3,338,992 A | 8/1967 | Kinney |
| 3,341,394 A | 9/1967 | Kinney |
| 3,381,688 A | 5/1968 | Satas |
| 3,494,821 A | 2/1970 | Evans |
| 3,502,538 A | 3/1970 | Petersen |
| 3,502,763 A | 3/1970 | Hartmann |
| 3,507,269 A * | 4/1970 | Berry ........................ 600/367 |
| 3,542,615 A | 11/1970 | Dobo et al. |
| 3,615,478 A | 10/1971 | Hoshino et al. |
| 3,650,754 A * | 3/1972 | Jones ....................... 430/270.1 |
| 3,692,618 A | 9/1972 | Dorschner et al. |
| 3,794,497 A | 2/1974 | Pratt et al. |
| 3,802,817 A | 4/1974 | Matsuki et al. |
| 3,836,633 A | 9/1974 | Bescke |
| 3,849,241 A | 11/1974 | Butin et al. |
| 3,919,437 A | 11/1975 | Brown et al. |
| 3,960,494 A | 6/1976 | Verma et al. |
| 3,971,665 A | 7/1976 | Suzuki et al. |
| 4,006,030 A | 2/1977 | Yoshida et al. |
| 4,041,203 A | 8/1977 | Brock et al. |
| 4,078,029 A | 3/1978 | Yoshida et al. |
| 4,100,324 A | 7/1978 | Anderson et al. |
| 4,101,638 A | 7/1978 | Inoue et al. |
| 4,144,370 A | 3/1979 | Boulton |
| 4,172,781 A | 10/1979 | Walk et al. |
| 4,297,233 A | 10/1981 | Gualandi |
| RE30,797 E | 11/1981 | Davis |
| RE30,803 E | 11/1981 | Davis |
| 4,313,820 A | 2/1982 | Farha, Jr. et al. |
| 4,340,563 A | 7/1982 | Appel et al. |
| 4,375,448 A | 3/1983 | Appel et al. |
| 4,407,960 A * | 10/1983 | Tratnyek ........................ 436/1 |
| 4,467,012 A | 8/1984 | Pedersen et al. |
| 4,469,746 A | 9/1984 | Weisman et al. |
| 4,488,969 A | 12/1984 | Hou |
| 4,494,278 A | 1/1985 | Kroyer et al. |
| 4,494,629 A | 1/1985 | Raeburn |
| 4,517,308 A | 5/1985 | Ehlenz et al. |
| 4,522,203 A | 6/1985 | Mays |
| 4,525,410 A | 6/1985 | Hagiwara et al. |
| 4,575,556 A | 3/1986 | Byrne et al. |
| 4,604,313 A | 8/1986 | McFarland et al. |
| 4,640,810 A | 2/1987 | Laursen et al. |
| 4,643,801 A | 2/1987 | Johnson |
| 4,655,757 A | 4/1987 | McFarland et al. |
| 4,701,218 A | 10/1987 | Barker et al. |
| 4,715,983 A | 12/1987 | Ota et al. |
| 4,725,415 A | 2/1988 | Kidd |
| 4,734,324 A | 3/1988 | Hill |
| RE32,649 E | 4/1988 | Brandt et al. |
| 4,775,585 A | 10/1988 | Hagiwara et al. |
| 4,780,448 A | 10/1988 | Broecker et al. |
| 4,781,858 A | 11/1988 | Mizukami et al. |
| 4,783,220 A | 11/1988 | Gamble et al. |
| 4,798,603 A | 1/1989 | Meyer et al. |
| 4,802,473 A | 2/1989 | Hubbard et al. |
| 4,818,464 A | 4/1989 | Lau |
| 4,823,404 A | 4/1989 | Morell et al. |
| 4,823,803 A | 4/1989 | Nakamura |
| 4,904,304 A | 2/1990 | Watanabe et al. |
| 4,969,457 A | 11/1990 | Hubbard et al. |
| 4,978,615 A | 12/1990 | Aoyama et al. |
| 4,988,505 A | 1/1991 | Watanabe et al. |
| 5,000,746 A | 3/1991 | Meiss |
| 5,020,533 A | 6/1991 | Hubbard et al. |
| 5,057,302 A | 10/1991 | Johnson et al. |
| 5,064,473 A | 11/1991 | Kubo et al. |
| 5,100,581 A | 3/1992 | Watanabe et al. |
| 5,100,702 A | 3/1992 | Maeda et al. |
| 5,108,739 A | 4/1992 | Kurihara et al. |
| 5,122,418 A | 6/1992 | Nakane et al. |
| 5,133,803 A | 7/1992 | Moffatt |
| 5,145,518 A | 9/1992 | Winnik et al. |
| 5,145,727 A | 9/1992 | Potts et al. |
| 5,169,706 A | 12/1992 | Collier, IV et al. |
| 5,178,931 A | 1/1993 | Perkins et al. |
| 5,183,656 A | 2/1993 | Uesaka et al. |
| 5,188,885 A | 2/1993 | Timmons et al. |
| 5,196,177 A | 3/1993 | Watanabe et al. |
| 5,204,429 A | 4/1993 | Kaminsky et al. |
| 5,209,998 A | 5/1993 | Kavassalis et al. |
| 5,220,000 A | 6/1993 | Theodoropulos |
| 5,221,497 A | 6/1993 | Watanabe et al. |
| 5,225,374 A | 7/1993 | Fare et al. |
| 5,230,953 A | 7/1993 | Tsugeno et al. |
| 5,238,518 A | 8/1993 | Okubi et al. |
| 5,245,117 A | 9/1993 | Withers et al. |
| 5,266,289 A | 11/1993 | Tsugeno et al. |
| 5,284,703 A | 2/1994 | Everhart et al. |
| 5,292,868 A | 3/1994 | Subramanian |
| 5,294,717 A | 3/1994 | Theodoropulos |
| 5,300,365 A | 4/1994 | Ogale |
| 5,322,061 A | 6/1994 | Brunson |
| 5,332,432 A | 7/1994 | Okubi et al. |
| 5,338,713 A | 8/1994 | Takagi et al. |
| 5,342,876 A | 8/1994 | Abe et al. |
| 5,350,624 A | 9/1994 | Georger et al. |
| 5,366,947 A | 11/1994 | Müller et al. |
| 5,382,400 A | 1/1995 | Pike et al. |
| 5,383,450 A | 1/1995 | Hubbard et al. |
| 5,397,667 A | 3/1995 | Law et al. |
| 5,407,442 A | 4/1995 | Karapasha |
| 5,407,600 A | 4/1995 | Ando et al. |
| 5,420,090 A | 5/1995 | Spencer et al. |
| 5,427,844 A | 6/1995 | Murai et al. |
| 5,429,628 A | 7/1995 | Trinh et al. |
| 5,451,450 A | 9/1995 | Erderly et al. |
| 5,458,864 A | 10/1995 | Tsugeno et al. |
| 5,472,775 A | 12/1995 | Obijeski et al. |
| 5,480,636 A | 1/1996 | Maruo et al. |
| 5,486,356 A | 1/1996 | Yim |
| 5,487,938 A | 1/1996 | Spencer et al. |
| 5,488,126 A | 1/1996 | Subramanian et al. |
| 5,527,171 A | 6/1996 | Soerensen |
| 5,538,548 A | 7/1996 | Yamazaki |
| 5,539,124 A | 7/1996 | Etherton et al. |
| 5,540,916 A | 7/1996 | Parks |
| 5,547,607 A | 8/1996 | Ando et al. |
| 5,553,608 A | 9/1996 | Reese et al. |
| 5,554,775 A | 9/1996 | Krishnamurti et al. |
| 5,580,655 A | 12/1996 | El-Shall et al. |
| 5,583,219 A | 12/1996 | Subramanian et al. |
| 5,591,797 A | 1/1997 | Barthel et al. |
| 5,597,512 A | 1/1997 | Watanabe et al. |
| 5,661,198 A | 8/1997 | Inatani et al. |
| 5,663,224 A | 9/1997 | Emmons et al. |
| 5,679,138 A | 10/1997 | Bishop et al. |
| 5,679,724 A | 10/1997 | Sacripante et al. |
| 5,695,868 A | 12/1997 | McCormack |
| 5,733,272 A | 3/1998 | Brunner et al. |
| 5,773,227 A | 6/1998 | Kuhn et al. |
| 5,795,985 A | 8/1998 | Hüsler et al. |
| 5,813,398 A | 9/1998 | Baird et al. |
| 5,817,300 A | 10/1998 | Cook et al. |
| 5,837,352 A | 11/1998 | English et al. |
| 5,843,509 A | 12/1998 | Calvo Salve et al. |
| 5,855,788 A | 1/1999 | Everhart et al. |
| 5,861,144 A | 1/1999 | Peterson et al. |
| 5,871,872 A | 2/1999 | Matijevic et al. |
| 5,874,067 A | 2/1999 | Lucas et al. |
| 5,880,176 A | 3/1999 | Kamoto et al. |
| 5,880,309 A | 3/1999 | Suzuki et al. |

| | | | | | | |
|---|---|---|---|---|---|---|
| 5,882,638 | A | 3/1999 | Dodd et al. | 6,607,711 | B2 | 8/2003 | Pedersen |
| 5,885,599 | A | 3/1999 | Peterson et al. | 6,623,848 | B2 | 9/2003 | Brehm et al. |
| 5,897,541 | A | 4/1999 | Uitenbroek et al. | 6,638,918 | B2 | 10/2003 | Davison et al. |
| 5,902,226 | A | 5/1999 | Tasaki et al. | 6,639,004 | B2 | 10/2003 | Falat et al. |
| 5,905,101 | A | 5/1999 | Fujiki et al. | 6,645,569 | B2 | 11/2003 | Cramer et al. |
| 5,916,596 | A | 6/1999 | Desai et al. | 6,693,071 | B2 | 2/2004 | Ghosh et al. |
| 5,948,398 | A | 9/1999 | Hanamoto et al. | 7,115,321 | B2 * | 10/2006 | Soerens et al. ............... 428/500 |
| 5,948,483 | A | 9/1999 | Kim et al. | 2001/0000889 | A1 | 5/2001 | Yadav et al. |
| 5,962,566 | A | 10/1999 | Grandfils et al. | 2001/0023338 | A1 | 9/2001 | Guarracino et al. |
| 5,964,926 | A | 10/1999 | Cohen | 2001/0031248 | A1 | 10/2001 | Hall-Puzio et al. |
| 5,972,389 | A | 10/1999 | Shell et al. | 2001/0056246 | A1 | 12/2001 | Rodriguez-Fernandez et al. |
| 5,985,229 | A | 11/1999 | Yamada et al. | 2002/0005145 | A1 | 1/2002 | Sherman |
| 5,989,510 | A | 11/1999 | Abe et al. | 2002/0006425 | A1 * | 1/2002 | Takaoka et al. ............. 424/405 |
| 5,989,515 | A | 11/1999 | Watanabe et al. | 2002/0066542 | A1 | 6/2002 | Jakob et al. |
| 6,004,625 | A | 12/1999 | Ohshima | 2002/0091071 | A1 | 7/2002 | Fischer et al. |
| 6,007,592 | A | 12/1999 | Kasai et al. | 2002/0106466 | A1 | 8/2002 | Hausmann et al. |
| 6,024,786 | A | 2/2000 | Gore | 2002/0110686 | A1 | 8/2002 | Dugan |
| 6,045,900 | A | 4/2000 | Haffner et al. | 2002/0128336 | A1 | 9/2002 | Kolb et al. |
| 6,047,413 | A | 4/2000 | Welchel et al. | 2002/0142937 | A1 | 10/2002 | Carter et al. |
| 6,057,162 | A | 5/2000 | Rounbehler et al. | 2002/0149656 | A1 | 10/2002 | Nohr et al. |
| 6,060,410 | A | 5/2000 | Gillberg-LaForce et al. | 2002/0150678 | A1 | 10/2002 | Cramer et al. |
| 6,073,771 | A | 6/2000 | Pressley et al. | 2002/0176982 | A1 | 11/2002 | Rohrbaugh et al. |
| 6,075,179 | A | 6/2000 | McCormack et al. | 2002/0177621 | A1 | 11/2002 | Hanada |
| 6,096,299 | A | 8/2000 | Guarracino et al. | 2002/0182102 | A1 | 12/2002 | Fontenot et al. |
| 6,111,163 | A | 8/2000 | McCormack et al. | 2003/0013369 | A1 | 1/2003 | Soane et al. |
| 6,149,952 | A * | 11/2000 | Horan ......................... 426/87 | 2003/0021983 | A1 | 1/2003 | Nohr et al. |
| 6,172,173 | B1 | 1/2001 | Spencer et al. | 2003/0050211 | A1 | 3/2003 | Hage et al. |
| 6,177,608 | B1 | 1/2001 | Weinstrauch | 2003/0056648 | A1 | 3/2003 | Fornai et al. |
| 6,190,814 | B1 | 2/2001 | Law et al. | 2003/0070782 | A1 | 4/2003 | Proverb et al. |
| 6,193,844 | B1 | 2/2001 | McLaughlin et al. | 2003/0082237 | A1 | 5/2003 | Cha et al. |
| 6,225,524 | B1 | 5/2001 | Guarracino et al. | 2003/0100842 | A1 | 5/2003 | Rosenberg et al. |
| 6,238,767 | B1 | 5/2001 | McCormack et al. | 2003/0130631 | A1 | 7/2003 | Springer et al. |
| 6,254,894 | B1 | 7/2001 | Denkewicz, Jr. et al. | 2003/0147956 | A1 | 8/2003 | Shefer et al. |
| 6,264,615 | B1 | 7/2001 | Diamond et al. | 2003/0147966 | A1 | 8/2003 | Franzen et al. |
| 6,277,346 | B1 | 8/2001 | Murasawa et al. | 2003/0181540 | A1 | 9/2003 | Quellet et al. |
| 6,277,772 | B1 | 8/2001 | Gancet et al. | 2003/0203009 | A1 | 10/2003 | MacDonald |
| 6,291,535 | B1 | 9/2001 | Watanabe et al. | 2003/0211618 | A1 * | 11/2003 | Patel ........................... 436/38 |
| 6,294,222 | B1 | 9/2001 | Cohen et al. | 2003/0235605 | A1 | 12/2003 | Lelah et al. |
| 6,299,867 | B1 | 10/2001 | Aoyagi et al. | 2004/0033269 | A1 | 2/2004 | Hei et al. |
| 6,309,736 | B1 | 10/2001 | McCormack et al. | 2004/0034157 | A1 | 2/2004 | Ghosh et al. |
| 6,315,864 | B2 | 11/2001 | Anderson et al. | 2004/0043688 | A1 | 3/2004 | Soerens et al. |
| 6,334,988 | B1 | 1/2002 | Gallis et al. | 2004/0122387 | A1 | 6/2004 | Long et al. |
| 6,344,218 | B1 | 2/2002 | Dodd et al. | 2004/0175556 | A1 | 9/2004 | Clark et al. |
| 6,344,272 | B1 | 2/2002 | Oldenburg et al. | 2005/0085739 | A1 * | 4/2005 | MacDonald et al. ........ 600/530 |
| 6,358,537 | B1 | 3/2002 | Hoshino et al. | | | | |
| 6,358,909 | B1 | 3/2002 | Ochomogo et al. | | | FOREIGN PATENT DOCUMENTS | |
| 6,369,290 | B1 | 4/2002 | Glaug et al. | | | | |
| 6,376,741 | B1 | 4/2002 | Guarracino et al. | EP | | 0232141 | 8/1987 |
| 6,387,495 | B1 | 5/2002 | Reeves et al. | EP | | 0251783 | 1/1988 |
| 6,398,827 | B1 | 6/2002 | Ota et al. | EP | | 0339461 | 11/1989 |
| 6,410,765 | B1 | 6/2002 | Wellinghoff et al. | EP | | 0348978 A2 | 1/1990 |
| 6,425,530 | B1 | 7/2002 | Coakley | EP | | 0376448 | 7/1990 |
| 6,427,693 | B1 | 8/2002 | Blackstock et al. | EP | | 0389015 | 9/1990 |
| 6,428,814 | B1 | 8/2002 | Bosch et al. | EP | | 0389023 | 9/1990 |
| 6,433,243 | B1 | 8/2002 | Woltman et al. | EP | | 0483500 A1 | 5/1992 |
| 6,440,187 | B1 | 8/2002 | Kasai et al. | EP | | 0510619 A1 | 10/1992 |
| 6,460,989 | B1 | 10/2002 | Yano et al. | EP | | 0282287 | 4/1996 |
| 6,461,735 | B1 | 10/2002 | Furuya et al. | EP | | 0972563 | 1/2000 |
| 6,467,897 | B1 | 10/2002 | Wu et al. | EP | | 0749295 | 7/2000 |
| 6,468,500 | B1 | 10/2002 | Sakaguchi et al. | EP | | 1034800 A1 | 9/2000 |
| 6,475,601 | B1 | 11/2002 | Sakaki et al. | EP | | 1053788 | 11/2000 |
| 6,479,150 | B1 | 11/2002 | Liu et al. | EP | | 1157672 | 11/2001 |
| 6,491,790 | B1 | 12/2002 | Proverb et al. | EP | | 1157672 A1 | 11/2001 |
| 6,498,000 | B2 | 12/2002 | Murasawa et al. | EP | | 1162172 A1 | 12/2001 |
| 6,517,199 | B1 | 2/2003 | Tomioka et al. | EP | | 1188854 A1 | 3/2002 |
| 6,531,704 | B2 | 3/2003 | Yadav et al. | EP | | 1214878 A1 | 6/2002 |
| 6,536,890 | B1 | 3/2003 | Kato et al. | EP | | 1216675 A1 | 6/2002 |
| 6,548,264 | B1 | 4/2003 | Tan et al. | EP | | 1298071 | 4/2003 |
| 6,551,457 | B2 | 4/2003 | Westman et al. | EP | | 1315526 B1 | 6/2003 |
| 6,562,441 | B1 | 5/2003 | Maeda et al. | JP | | 62149322 | 7/1987 |
| 6,575,383 | B2 | 6/2003 | Dobler et al. | JP | | 3221142 | 9/1991 |
| 6,578,521 | B2 | 6/2003 | Raymond et al. | WO | | WO 8902698 A1 | 4/1989 |
| 6,589,562 | B1 | 7/2003 | Shefer et al. | WO | | WO 91/12030 * | 8/1991 |

| | | | |
|---|---|---|---|
| WO | WO 9111977 A1 | 8/1991 |
| WO | WO 9112029 A1 | 8/1991 |
| WO | WO 9112030 A1 | 8/1991 |
| WO | WO 9619346 A2 | 6/1996 |
| WO | WO 9619346 A3 | 6/1996 |
| WO | WO 9705482 A1 | 2/1997 |
| WO | WO 9725076 A1 | 7/1997 |
| WO | WO 98/20915 | 5/1998 |
| WO | WO 9820915 A1 | 5/1998 |
| WO | WO 98/26808 | 6/1998 |
| WO | WO 9826808 A2 | 6/1998 |
| WO | WO 9826808 A3 | 6/1998 |
| WO | WO 99/47252 | 9/1999 |
| WO | WO 00/03797 | 1/2000 |
| WO | WO 0013764 A1 | 3/2000 |
| WO | WO 0029036 A2 | 3/2000 |
| WO | WO 0029036 A3 | 3/2000 |
| WO | WO 0059555 A1 | 10/2000 |
| WO | WO 00/76558 | 12/2000 |
| WO | WO 0076558 A1 | 12/2000 |
| WO | WO 01/06054 | 1/2001 |
| WO | WO 02/26272 | 4/2002 |
| WO | WO 02/49559 | 6/2002 |
| WO | WO 02/055115 | 7/2002 |
| WO | WO 02/062881 | 8/2002 |
| WO | WO 02/064877 | 8/2002 |
| WO | WO 02/083297 | 10/2002 |
| WO | WO 02/084017 | 10/2002 |
| WO | WO 02/095112 | 11/2002 |
| WO | WO 02094329 A1 | 11/2002 |
| WO | WO 03/000979 | 1/2003 |
| WO | WO 03/025067 | 3/2003 |
| WO | WO 03032959 A1 | 4/2003 |
| WO | WO 03088931 A2 | 10/2003 |
| WO | WO 03/092885 | 11/2003 |
| WO | WO 2004000986 A1 | 12/2003 |

OTHER PUBLICATIONS

Jun. 1995 BOC Gases Ethylene Oxide MSDS.*
Baker, M. E. J. and Ramaier, N., "Development of an optical formaldehyde sensor based on the use of immobilized pararosaniline," Analyst, 1994, 119(5), abstract.*
Quincy, III, et al., U.S. Appl. No. 10/723,761, filed Nov. 26, 2004, Ordor Control In Personal Care Products.
MacDonald, et al., U.S. Appl. No. 10/955,316, filed Sep. 30, 2004, Ordor-Reducing Quinone Compounds.
Abstract of Japanese Patent No. JP04255767, Sep. 10, 1992.
Abstract of Japanese Patent No. JP05098185, Apr. 20, 1993.
Abstract of Japanese Patent No. JP57135360, Aug. 20, 1982.
Abstract of Japanese Patent No. JP2001208753, Mar. 8, 2001.
Abstract of Japanese Patent No. JP198610366, Jan. 11, 1986.
Article—A sorbent tube for oral malodour monitoring, Julia Rodríguez-Fernández, Regina López-Fernández, Rosario Pereiro, Manuel Menéndez, José María Tejerina, Alberto Sicilia, and Alfredo Sanz-Medel, Talanta, vol. 62, 2004, pp. 421-426.
Article—Optical fibre sensor for hydrogen sulphide monitoring in mouth air, Julio Rodríguez-Fernández, Rosario Pereiro, and Alfredo Sanz-Medel, Analytica Chimica Acta, vol. 471, 2002, pp. 13-23.
Abstract of Japanese Patent No. JP1262868, Oct. 19, 1989.
Abstract of Japanese Patent No. JP2157039, Jun. 15, 1990.
Abstract of Japanese Patent No. JP3195562, Aug. 27, 1991.
Abstract of Japanese Patent No. JP4335141, Nov. 24, 1992.
Abstract of Japanese Patent No. JP5261246, Oct. 12, 1993.
Abstract of Japanese Patent No. JP6285140, Oct. 11, 1994.
Abstract of Japanese Patent No. JP63072337, Apr. 2, 1988.
Abstract of Japanese Patent No. JP8152409, Jun. 11, 1996.
Annex to Form PCT/ISA/206 for PCT/US2004/027624, Dec. 8, 2004.
Abstract of SU834073, May 30, 1981.
PCT Search Report and Written Opinion for PCT/US2004/011596, Aug. 30, 2004.
PCT Search Report and Written Opinion for PCT/US2004/016933, Nov. 2, 2004.
Article—Immunization of mice with peptomers covalently couopled to aluminum oxide nanoparticles, Andreas Frey, Nicholas Mantis, Pamela A. Kozlowski, Alison J. Quayle, Adriana Bajardi, Juana J. Perdomo, Frank A. Robey, and Marian R. Neutra, Vaccine, vol. 17, 1999, pp. 3007-3019.
PCT Search Report for PCT/US03/39737, Jun. 18, 2004.
Abstract of Japanese Patent No. 7256025, Oct. 9, 1995.
PCT Search Report for PCT/US03/32846, Jun. 7, 2004.
Article—Adsorption of Dyes on Nanosize Modified Silica Particles, Guangwei Wu, Athanasia Koliadima, Yie-Shein Her, and Egon Matijevic, Journal of Colloid and Interface Sciences, vol. 195, 1997, pp. 222-228.
Article—Adsorption of Proteins and Antibiotics on Porous Alumina Membranes, Yi Hua Ma, Aseem Bansal, and William M. Clark, Fundamentals of Adsorption, vol. 80, 1992, pp. 389-396.
Product Information Sheet for Snowtex®, 6 pages.
Article—Significance of Ammonia in the Genesis of Gastric Epithelial Lesions Induced by Helicobacter pylori: An in vitro Study with Different Bacterial Strains and Urea Concentrations, P. Sommi, V. Ricci. R. Fiocca, M. Romano, K.J. Ivey. E. Cova, E. Solcia, and U. Ventura, Digestion, vol. 57, 1996, pp. 299-304.
Article—Ammonia vapour in the mouth as a diagnostic marker for Helicobacter pylori infection: preliminary "proof of principle" pharmacological investigations, C. D. R. Dunn, M. Black, D. C. Cowell, C. Penault, N. M. Ratcliffe, R. Spence, and C. Teare, British Journal of Biomedical Science, vol. 58, 2001, pp. 66-76.
Article—Purification and Characterization of Urease from Helicobacter pylori, Bruce E. Dunn, Gail P. Campbell, Guillermo I. Perez-Perez, and Martin J. Blaser, The Journal of Biological Chemistry, vol. 265, No. 16, Jun. 5, 1990, pp. 9464-1990.
Article—Validation of $^{13}C$-Urea Breath Test for the Diagnosis of Helicobacter pylori Infection in the Singapore Population, T. S. Chua, K. M. Fock, E. K. Teo, T. M. Ng, Singapore Medical Journal, vol. 43, No. 8, 2002, pp. 408-411.
Article—Significance of ammonia produced by Helicobacter pylori, Shigeji Ito, Yoshihiro Kohli, Takuji Kato, Yoshimichi Abe, and Takashi Ueda, European Journal of Gastroenterology & Hepatology, vol. 6, No. 2, 1994, pp. 167-174.
Article—Spectrophotometric Assay of Thiols, Peter C. Jocelyn, Methods in Enzymology, vol. 142, 1987, pp. 44-67.
Derwent Abstract, JP 5106199A, Apr. 1993, Nakajima et al.
Derwent Abstract, JP 9143872A, Jun. 1997, Sogawa.
Brunauer, S. et al., "Adsorption of Gases in Multimolecular Layers", Journal of American Chemical Society, vol. 60, Feb. 1938, pp. 309-319.
Béné, A. et al., "Applicability of a SPME Method for the Rapid Determination of VOCs", Chimia, 56, No. 6, 2002, ISSN 0009-4293, pp. 289-291.
Malik, D.J. et al., "Characterisation of Novel Modified Active Carbons and Marine Algal Biomass for the Selective Adsorption of Lead", Water Research, 36, 2002, pp. 1527-1538.
Cost, F., Pocket Guide to Digital Printing, Delmar Publishers, Albany, NY, ISBN 0-8273-7592-1, pp. 144-145, Jul. 1996.
Noller, C.R., "Saponins and Sapogenins. VIII. Surface Films of Echinocystic Acid and Derivatives", The Journal of the American Chemical Society, vol. 60, 1938, 3 pages.
Maldotti, A. et al., "Immobilization of $(n-Bu_4N)_4W_{10}O_{32}$ on Mesoporous MCM-41 and Amorphous Silicas for Photocatalytic Oxidation of Cycloalkanes with Molecular Oxygen", Journal of Catalysis, vol. 209, 2002, pp. 210-216.
Zhang, Q. et al., "Fe-MCM-41 for Selective Epoxidation of Styrene with Hydrogen Peroxide", The Chemical Society of Japan, Chemistry Letters 2001, pp. 946-947.
Melde, B.J. et al., "Mesoporous Sieves with Unified Hybrid Inorganic/Organic Frameworks", Chem. Mater., vol. 11, No. 11, 1999, pp. 3302-3308.

Polarz, S. et al., "From Cyclodextrin Assemblies to Porous Materials by Silica Templating", *Angew. Chem. Int. Ed.*, vol. 40, No. 23, 2001, pp. 4417-4421.

Shi, D. et al., "Uniform Deposition of Ultrathin Polymer Films on the Surfaces of $Al_2O_3$ Nanoparticles by a Plasma Treatment", University of Cincinnati and University of Michigan, Jun. 2000, pp. 1-15.

Santra, S. et al., "Development of novel dye-doped silica nanoparticles for biomarker application", *Journal of Biomedical Optics*, vol. 6, No. 2, Apr. 2001, pp. 160-166.

Buchhammer, M. et al., "Nanoparticles based on polyelectrolyte complexes: effect of structure and net charge on the sorption capacility for solved organic molecules", *Colloid Polym. Sci.*, vol. 278, 2000, pp. 841-847.

Brunauer, S. et al., "Adsorption of Gases in Multimolecular Layers", *The Journal of the American Chemical Society*, vol. 60, Feb. 1938, pp. 309-319.

Schaber, P.M. et al., "Study of the urea thermal decomposition (pyrolsis) reaction and importance to cyanuric acid production", *American Laboratory*, Aug. 1999, pp. 13-21.

Bergna, H.E., Editor, "Silanol Groups, Siloxane Bridges, and Physically Adsorbed Water", The Colloid Chemistry of Silica, American Chemical Society $200^{th}$ National Meeting, Aug. 26-31, 1990, pp. 22-23 and pp. 52-59.

Schweigert, I.V. et al., "Structure and properties of silica nanoclusters at high temperatures", *The American Physical Society*, Physical Review B, vol. 65, No. 235410, pp. 1-9, May 28, 2002.

Biermann, C.J. et al., Grafting of Poly(ethylenimine) onto Mesylated Cellulose Acetate, Poly(methyl methacrylate) and Poly(vinyl chloride), *Carbohydrate Polymers*, vol. 12, 1990, pp. 323-327.

Yurieva, T.M. et al., Abstract of "Non-hydrothermal synthesis of copper-, zinc- and copper-zinc hydrosilicates", *Materials Research Innovations*, vol. 5, No. 1, Jun. 2001, 2 pages.

* cited by examiner

ODOR CONTROLLING ARTICLE INCLUDING A VISUAL INDICATING DEVICE FOR MONITORING ODOR ABSORPTION

BACKGROUND OF THE INVENTION

The present invention generally relates to a visual indicating device for use in articles that control and absorb odors, and in particular, odors such as foot odor, urine odor, feces odor, garbage odor, tobacco odor and raw meat odor. The invention also relates to an odor absorbent article including such an indicating device.

Several products have been developed for odor control, most of which are based on odor masking, odor absorption or the degradation of odor forming compounds. In products where the odor is controlled through odor absorption, the user generally has no idea as to whether the odor absorbing article is working or not, other than by the slow removal of the offending odor. Thus, when the odor absorbing product has become saturated and needs to be replaced, the user would only become aware of this when the product stops absorbing the odor and the offending odor becomes noticeable. It would therefore be advantageous for the user to be made aware of the fact that the article was saturated and needed replacing prior to this situation arising.

In some situations it would also be advantageous if the user could be made aware that a odor is present, even though it was being absorbed and was not noticeable, so that the user could take steps to remove the cause of the odor, or could feel more at ease that the product was working efficiently.

U.S. Pat. No. 5,733,272 to Brunner et al. teaches the use of a fragrance or perfume to indicate that an odor is being removed. This fragrance is moisture-activated, and the scent is released in small bursts when wetted. U.S. Pat. No. 6,369,290 to Glaug et al. and PCT International Publication No. WO 98/26808 to Trinh also disclose the release of a fragrance to indicate that an odor is being removed.

However, the use of a fragrance is not always desirable, as not all users will find a fragrance to be pleasant, and there may be situations where the user would prefer the indicator to be a discreet type of indicator, rather than the release of a fragrance which could be detected by others. Such a system also does not indicate to the user when the odor absorbing product is saturated and needs to be replaced.

EP Patent No. 1 157 672 to Carlucci et al. discloses a liquid and odor absorbent structure for inanimate places such as refrigerators. The patent mentions that the structure may be provided with an indicator to indicate the end of the life time of the structure, but goes no further than this in regard to the indicator, except to mention that the indicator would be a conventional indicating means known to those skilled in the art.

PCT International Publication No. WO 00/76558 to Persson describes the use of a visual indicator to indicate the activity of an active ingredient in an absorbing article. The visual indicator changes color in response to a change in the active additive in the absorbing article. This change in the activity of the active additive could be as a result of a number of reasons, for example a change in the environmental conditions.

The inventors are not aware of any existing visual indicating system which is suitable for use on an odor absorbent product and which changes color in direct response to an odor.

SUMMARY OF THE INVENTION

The invention provides an article for controlling a odor, the article comprising an odor absorbing agent and at least one visual indicating agent that changes color in response to the odor. Depending on the concentration of the indicating agent, the color change will be observed when the odor is present, when the odor is being absorbed or when the odor absorbing article is saturated and needs to be replaced.

As used herein the terms "odorous compound", "odor" and "odor" refer to any molecule or compound detectable to the olfactory system. Odorous compounds can exist as gaseous compounds and can also be present in other media such as liquid.

As used herein the term "odor absorbing agent" refers to a substance, compound, chemical, mixture or absorbent (such as activated carbon, clay, zeolites, coated or modified nanoparticle silica or alumuina and molecular sieves) useful in controlling odors.

As used herein the term "visual indicating agent" refers to a substance, a composition or a material that gives a visual indication when a odor is present in a sufficient concentration.

The visual indicating agent is typically color-sensitive to at least one odors selected from the group comprising body odor, foot odor, garbage odor, urinary odor, feces odor, tobacco odor, raw meat odor, other common household odors such as bathroom, pet and cooking odors, mercaptans (or thiols), amines, ammonia, sulfur, sulfides, hydrogen sulphide, sulfur degradation products, aliphatic acids, isovaleric acid, butyric acid, and acetic acid.

Suitable visual indicating agents are selected from neutral red, 3-nitrophenol, brilliant yellow, chlorophenol red, Rose Bengal dye, D&C red 28 dye, 4,4'-bis(dimethylamino)-benzhydrol (BDMB or Michler's hydrol (MH)), methyl red, methyl violet, methyl orange, bromocresol mauve, Acid Blue 80, blue dye Calcocid Blue 2G, ethyl red, bromophenol blue, bromocresol green, crystal violet, cresol red, thymol blue, erythrosine B, 2,4-dinitrophenol, Eriochrome™ Black T, alizarin, bromothymol blue, phenol red, m-nitrophenol, o-cresolphthalein, thymolphthalein, alizarin Yellow Reller, cobalt salts and complexes, copper salts and complexes, copper phenanthroline complexes and iron salts and complexes.

Additional indicating agents are those represented by the following general formula (I) or (II):

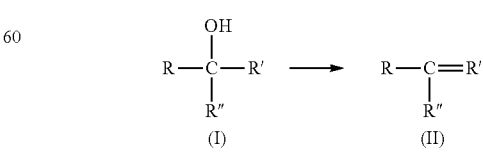

where R, R' and R" are as shown in Table 1:

TABLE 1

Indicating agents having the general formula (I) or (II)

| Indicating Agent | R | R" | R' | Indicating Agent for |
|---|---|---|---|---|
| Michler's Hydrol (MH) | H | $(CH_3)_2NC_6H_4$ | $(CH_3)_2NC_6H_4$ | Thiols, Mercaptans, Ammonia, Amines, Diamines and Polyamines |
| Pararosaniline (PAB) | $(NH_2)C_6H_4$ | $(NH_2)C_6H_4$ | $(NH_2)C_6H_4$ | Ammonia, Amines, Diamines and Polyamines |
| Alpha-naphtholbenzein (ANB) | $C_6H_5$ | \[structure: OH-naphthyl—=naphthyl=O\] | | Ammonia, Amines, Diamines and Polyamines |
| Naphthochrome Green (NCG) | $C_6H_5$ | \[structure: $NaO_2C$, OH-naphthyl—=naphthyl($CO_2Na$)=O\] | | Ammonia, Amines, Diamines and Polyamines |

The odor absorbing agent is typically activated charcoal, sodium bicarbonate, clay, zeolites, silicates, starches, ion exchange resins, cyclodextrins, molecular sieves or high surface area materials such as nanoparticles (see, for example, EP-A-348 978, EP-A-510619, WO 91/12029, WO 91/11977, WO 89/02698 and WO 91/12030).

In some instances, the visual indicating agent and odor absorbing agent may be the same agent. For example, BDMB may be used as both the odor absorbing agent and the visual indicating agent for sulfur, amine and ammonia odors.

Suitable odor absorbing articles to which the visual indicating agent may be applied include without limitation disposable diapers, training pants, undergarment pads, sanitary napkins, tampons, panty shields, incontinence pads, absorbent underpants, baby wipes, absorbent tissues, medical garments, bandages, absorbent drapes, medical wipes, face masks, air filtration media, air freshener products, disposable odor absorbing sheets for shoes, gym bags, lockers or garbage areas and so forth.

The visual indicating agent is applied to the article on a strip or patch attached to or printed on the odor absorbing article, and may be applied in a pattern such as a plurality of zones, dots, stripes, a circular shape or text that appears, fades or changes color when the visual indicating agent changes color. The patch or strip can be applied as a coating on any fabric or film layer, such as the breathable film of an outer cover of a disposable diaper, on the outer cover of an air freshening product or on a sheet for absorbing foot odor.

The visual indicating agent may be applied to the article in solution and allowed to dry so that a dried residue remains on the article. As used herein, the term "solution" refers to the indicating agent in a liquid such as water, an aqueous solution, alcohol, toluene and the like.

The device may include a single zone with a concentration of the indicating agent such that the indicating agent and hence the zone will change color to indicate that an odor absorbing device has reached saturation point and should be replaced.

However, as the concentration of the indicating agent and the amount of odor are the major factors determining the time in which the indicating agent takes to change color, the use of zones having different concentrations of the indicating agent allows a graduated scale to be produced that would indicate to the user that the odor absorbing article to which the strip or patch was applied was working and how much of the odor absorbing capacity was left (or conversely, how much of the absorbing article is used up). The final color or lack of color indicates when the absorbing article is saturated and needs to be replaced. The scale may be in the form of a linear scale, a circular scale, a collection of dots, text and so forth.

DETAILED DESCRIPTION OF THE INVENTION

Figure 1:
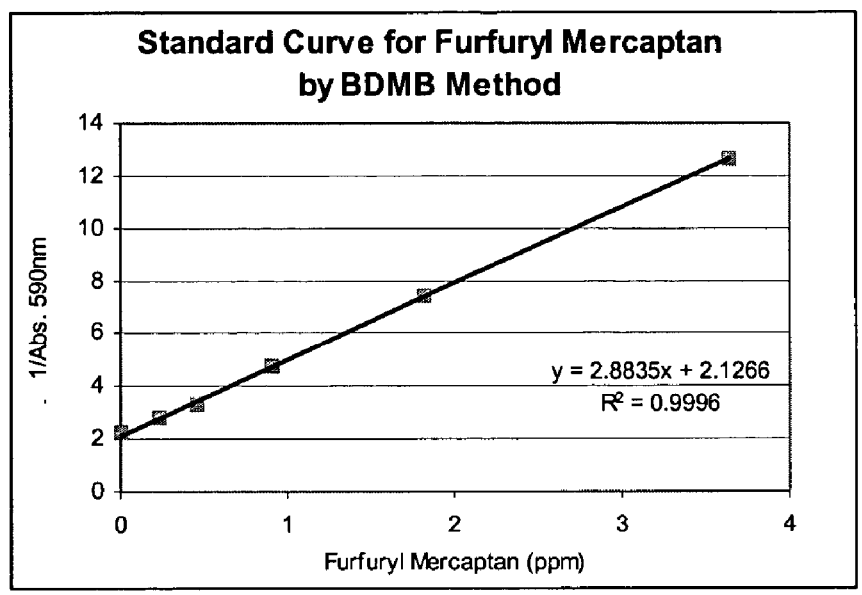
FIG. 1 shows a standard curve for the detection of furfuryl mercaptan by 4,4'-bis(dimethylamino)-benzhydrol (BDMB)

There is currently no suitable system of visually indicating to a user when an odor absorption device has detected an odor and/or when the odor absorption device is saturated and needs to be replaced.

It would be advantageous to a user of odor absorption articles, and in particular urine odor, feces odor, body odor, foot odor and other common household odors, if the odor absorption article included an indicator for visually indicating when an odor is present and/or when the article has reached a saturation point and needs to be replaced.

Thus, the invention provides a visual indicating device for visually indicating when an odor absorbing article is saturated.

The major odorous components of common household odors, such as cat odor, dog odor, garbage odor, body odor, foot odor, food odor, urine odor, feces odor, and tobacco odor are amines, sulfur compounds, carboxylic acids and aldehydes.

For example, the generation of odor from urine is mostly based on chemical and biological degradation of urine components, and amines, ammonia and sulfur degradation products (methyl mercaptan and hydrogen sulfide) are the major odor sources in urine. They can also be found in feces odor and body odor. Additionally, enzymes such as urease can convert urea, a major component in urine, to ammonia and thereby increase the generation of odors in urine. Aliphatic acids such as valeric, isovaleric, butyric and acetic acids are commonly found to be the major odor components in body odors, foot odor, tobacco smoke, raw meat, garbage (kitchen) odor, cat odor and the musty smell of basements and cellars.

Table 2 shows the concentration of the chemical components of common household odors along with their human threshold values (concentration that can be detected by the human nose).

TABLE 2

Concentration of the chemical components of common household odors along with their human threshold values

| Odor | Major Chemical Components | Concentration (ppb) | Human Threshold (ppb) |
|---|---|---|---|
| Dog odor | Ammonia | 5900 | 1500 |
|  | Trimethylamine | 1500 | 0.03 |
|  | Methyl mercaptan | 0.5 | 0.07 |
| Cat odor | n-Butyric acid | 0.3 | 0.19 |
|  | Ammonia | 1980 | 1500 |
|  | Trimethylamine | 0.3 | 0.03 |
| Garbage odor | Methyl mercaptan | 56 | 0.07 |
|  | n-Butyric acid | 166 | 0.19 |
|  | n-Valeric acid | 52 | 0.04 |
| Sock odor (foot) | iso-Valeric acid | 1.36 | 0.08 |
|  | n-Valeric acid | 0.1 | 0.04 |
|  | Hydrogen sulfide | 0.7 | 0.41 |
| Cooking odor - Fish | Acetaldehyde | 1740 | 1.50 |
|  | Dimethyl sulfide | 41 | 3.0 |
|  | Hydrogen sulfide | 11 | 0.41 |
| Cooking odor - Shrimp | Acetaldehyde | 15 | 1.5 |
|  | trimethylamine | 96 | 0.03 |
|  | Hydrogen sulfide | 11 | 0.41 |
| Cooking odor - Chicken breast | Carbon disulfide | 283 | 0.5 |
| Bathroom odor - Urine | Methyl mercaptan | 0.07 | 0.06 |
|  | Hydrogen sulfide | 32 | 0.41 |
| Bathroom odor - Feces | Hydrogen sulfide | 32 | 0.41 |
|  | Methyl mercaptan | 2.3 | 0.07 |
|  | Acetic acid | 29.7 | 6.0 |

In the examples which follow, several color changing indicating agents that are sensitive to very low levels (for example>0.01 parts per billion (ppb), more preferably from >10 ppb, and most preferably >100 ppb) of amines, ammonia, sulfur compounds, carboxylic acids and aldehydes were identified (Table 3). While the indicating agent may not detect the lower levels of odorous compounds immediately, it may change color in response to these low levels over a period of time, which may be hours (for example, in the case of a diaper), days, weeks or even months (such as in an air filter). The indicating agents are all available from Aldrich Chemical Co. of Milwaukee, Wis.

Michler's Hydrol reacts with amine or sulfur compounds according to the following reaction:

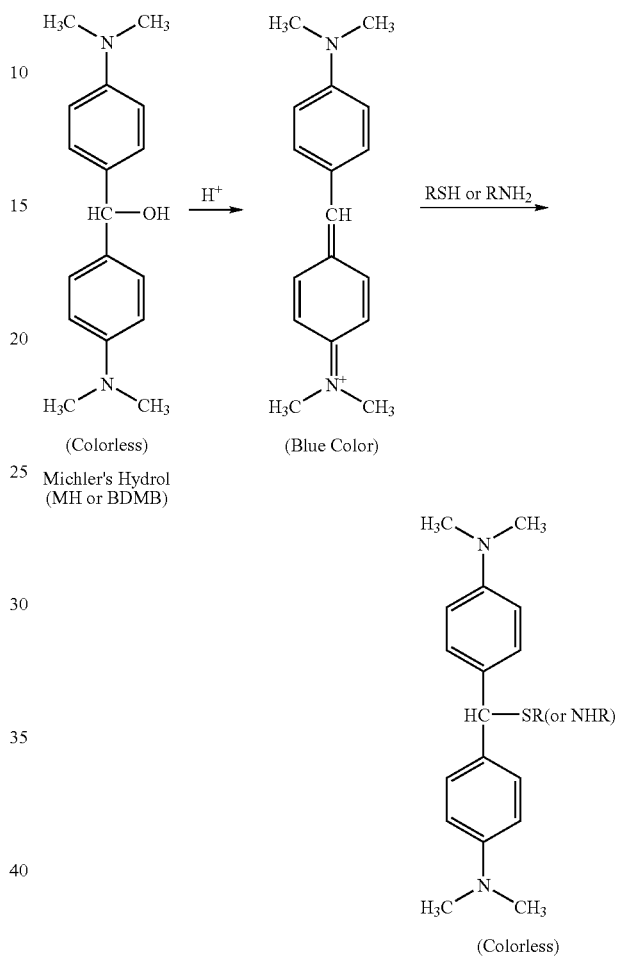

Michler's Hydrol
(MH or BDMB)

Although the odor absorbing agents which are specifically mentioned in the examples below are nanoparticles from Nissan Chemical America Corporation of Houston, Tex. and Michler's Hydrol from Aldrich Chemical, other odor absorbing agents such as activated charcoal, sodium bicarbonate, clay, zeolites and molecular sieves, which are known in the art, and other high surface area materials or nanoparticles may also be used as the odor absorbing agent.

The nanoparticles used in the practice of this invention can act as carriers for at least one metal ion present on the surface of the nanoparticle, and the metal ion creates an active site that binds with at least one gaseous compound and/or odorous compound thereby removing the compound from the surrounding environment. Nanoparticles can also absorb certain gaseous compounds and/or odorous compounds from the surrounding environment by adsorption directly onto the surface of the nanoparticles.

The nanoparticles are modified with metal ions that ionically bond with compounds such as gases and odorous compounds. "Metal ion" refers to salt ions and/or ion complexes of transition metal elements designated as IB through VIIIB on the periodic table. Other ions can be used in the invention as well. The nanoparticle may be made from any of silica, alumina, magnesium oxide, titanium dioxide, iron oxide, gold, zinc oxide, copper oxide, and combinations thereof, and may have thereon at least one metal ion of copper ion, silver ion, gold ion, permanganate ion, chlorite ion, persulfate ion, iron ion, and combinations thereof.

Modified nanoparticles are made by mixing nanoparticles with solutions containing metal ions. Such solutions are generally made by dissolving metallic compounds into a solvent, resulting in free metal ions in the solution. The metal ions are drawn to and adsorbed onto the nanoparticles due to the electric potential differences. Further discussion of the modification of nanoparticles may be found in U.S. patent application Ser. No. 10/137,052, filed on Apr. 30, 2002, which is incorporated by reference.

It is also possible to bond metal and silica particles to form a "coordinate" and/or "covalent bond." This may have a variety of benefits, such as reducing the likelihood that any of the metal will remain free during use (e.g., after washing). Strong adherence of the metal to the silica particles, further, also optimizes odor adsorption effectiveness.

Numerous techniques may be utilized to form a stronger bond between the transition metal and silica particles. Silica sols, for example, are generally considered stable at a pH of greater than about 7, and particularly between a pH of 9-10. When dissolved in water, salts of transition metals are acidic (e.g., copper chloride has a pH of approximately 4.8). Thus, when such an acidic transition metal salt is mixed with a basic silica sol, the pH is lowered and the metal salt precipitates on the surface of the silica particles. This compromises the stability of the silica particles. Further, at lower pH values, the number of silanol groups present on the surface of the silica particles is reduced. Because the transition metal binds to these silanol groups, the capacity of the particles for the transition metal is lowered at lower pH values.

In order to ameliorate the pH-lowering affect caused by the addition of an acidic transition metal salt (e.g., copper chloride), certain embodiments of the present invention employ selective control over the pH of the silica particles during mixing with the transition metal. The selective control over pH may be accomplished using any of a variety of well-known buffering systems known in the art.

The use of pH control in the modification of silica nanoparticles was demonstrated using a 10 weight percent suspension of SNOWTEX-OXS® nanoparticles from Nissan Chemical, having an unmodified particle size of 4 to 6 nm. The pH of the solution was adjusted to 8.7 and then added to a solution of copper chloride with high mixing shear (about 10,000 rpm). The pH, Zeta potential and particle size were monitored and when a positive Zeta potential was obtained the addition of copper chloride was stopped. The resulting copper modified nanoparticle had a particle size of about 43 nm and a surface area of about 500 square meters per gram.

Other techniques may also be utilized to further enhance the strength of the bonds formed between the transition metal and the silica particles.

Coupling agents in an effective amount may be used to link the transition metal to the silica particle, for example. Such coupling agents may be employed with or without the pH adjustment discussed above. In some cases, an organofunctional silane coupling agent may be used to link the transition metal to the silica particles. Some examples of suitable organofunctional silane coupling agents that may be used include, but are not limited to, vinyltrichlorosilane, vinyltrimethoxysilane, vinyltriethoxysilane, vinylmethyldichlorosilane, vinylmethyldimethoxysilane, vinylmethyldiethoxysilane, 5-hexenyltrimethoxysilane, 3-glycidoxypropyltrimethoxysilane, 3-glycidoxypropyltriethoxysilane, 3-glycidoxypropylmethyldimethoxysilane, 3-glycidoxypropylmethyldiethoxysilane, 3-(meth)acryloxypropyltrimethoxysilane, 3-(meth)acryloxypropyltriethoxysilane, 3-(meth)acryloxypropylmethyldimethoxysilane, 3-(meth)acryloxypropylmethyldiethoxysilane, 4-vinylphenyltrimethoxysilane, 3-(4-vinylphenyl)propyltrimethoxysilane, 4-vinylphenylmethyltrimethoxysilane, 3-aminopropyltrimethoxysilane, 3-aminopropyltriethoxysilane, 3-aminopropylmethyldimethoxysilane, 3-aminopropylmethyldiethoxysilane, 3-(2-aminoethyl)aminopropyltrimethoxysilane, 3-mercaptopropyltrimethoxysilane, 3-mercaptopropyltriethoxysilane, 3-mercaptopropylmethyldimethoxysilane, 3-mercaptopropylmethyldiethoxysilane, and partial hydrolyzates thereof.

Of these coupling agents, organofunctional alkoxysilanes, and particularly aminofunctional alkoxysilanes (e.g., 3-aminopropyltriethyoxysilane), are preferred.

Generally speaking, the silane coupling agents may be covalently linked to the silica particles through the silanol groups (Si—OH) present on the surface thereof. Specifically, the silicon atom of the silane coupling agent may form a covalent bond with the oxygen of the silanol group. Once the silane coupling agent is covalently linked to the silica particles, the organofunctional group may form a coordinate bond with the transition metal. Copper, for example, may form a coordinate bond with different amino groups present on aminopropyltriethoxysilane coupling agents.

The quantity of odor absorbing agent used in the odor absorbing article will depend on the nature of the article and amount of odor it is intended to absorb, and will therefore vary from article to article. For example, a disposable diaper which is intended to absorb urine and feces odors may contain a different amount of odor to a sheet intended to absorb pet odor over a longer period of time. By measuring the odor absorption capacity of the sheet or article (mg odor absorbable/gram of sheet) and knowing that the indicating agent reacts with the odor compound (mole of odor compound/mole of indicating agent), the odor absorption capacities can be matched to tune the indicating agent to the odor absorption of the sheet or article. Thus, without intending to limit the invention in any way, the indicating agent may be present in an amount of from 0.001 to 15% wt/wt, more preferably from 0.005 to 5% wt/wt, and most preferably from 0.1 to 1% w/wt. As the amount of indicating agent used in the invention will depend on the amount of odor which can be absorbed by the article, the concentration of indicating agent which is applied to the article will also vary according to the article.

TABLE 3

Visual indicating agents and the specific odors that cause color change

| Visual Indicating Agent | Odor or Odor Class |
| --- | --- |
| Michler's Hydrol | Ammonia, amines, sulfur compounds |
| Copper salts and complexes | Ammonia, amines, sulfur compounds |
| Rose Bengal (Acid Red 94) | Sulfur compounds |
| D&C Red 28 (Acid Red 92) | Sulfur compounds |
| Cobalt salts and complexes | Sulfur compounds, aldehydes, amines |
| Copper phenanthroline | Sulfur compounds and amines |
| Iron salts and complexes | Sulfur compounds and amines |
| Phenol red | Aliphatic carboxylic acids |
| Cresol red | Aliphatic carboxylic acids |
| Neutral red | Aliphatic carboxylic acids |
| 3-Nitrophenol | Aliphatic carboxylic acids |
| Brilliant Yellow | Aliphatic carboxylic acids |
| Bromothymol blue | Aliphatic carboxylic acids |
| Chlorophenol red | Aliphatic carboxylic acids |
| Pararosaniline base | Ammonia and amines |

TABLE 3-continued

Visual indicating agents and the specific odors that cause color change

| Visual Indicating Agent | Odor or Odor Class |
|---|---|
| Alpha-naphtholbenzene | Ammonia and amines |
| Naphthochrome green | Ammonia and amines |

In the examples which follow, a color-changing visual indicating agent was dissolved in a solvent (e.g. water, alcohol or acetonitrile) to give a concentration in the range of from 1 mg/ml to 100 mg/ml. The solution was then applied to a substrate (e.g. cellulose, cotton, nonwoven, glass fiber) by one of the following methods:
- (a) dropping known amounts of the solution onto the surface of the substrate, allowing the liquid to wet the substrate, and then allowing the substrate to air-dry;
- (b) dipping the substrate into the solution, nipping it to remove the excess solution and then air-drying or oven-drying the substrate in a low temperature oven;
- (c) spraying the solution onto the substrate and allowing it to dry; or
- (d) printing the solution onto the substrate by flexographic, off-set or inkjet printing.

The substrate was optionally pre-coated with an odor absorbing agent before the visual indicating agent was applied.

Samples containing the visual indicating agent were tested by placing the sample into a jar with 2 cm×2 cm cellulose tissue which had been impregnated with 2 drops of an odor solution (25 mg odor in 25 ml of solution). A lid was placed onto the container and the time and completeness of the color change observed.

EXAMPLE 1

A dilute solution of isovaleric acid (a major foot odor component) available from Aldrich Chemical was prepared by adding 25 mg of the acid to 50 ml of deionized water and stirring for 30 minutes in a sealed container. This was used as an odor standard to mimic foot odor.

An odor absorbing coating was applied onto a Scott® paper towel, available from Scott Paper of Mississauga, ON, Canada via a dip and air-dry method. The odor absorbing agents for this example were alumina-coated silica nanoparticles SNOWTEX-AK®, available from Nissan Chemical.

A visual indicating agent, phenol red (also available from Aldrich Chemical) was added in solution (10 mg/ml) by placing 1 to 5 drops of the solution onto the towel and allowing it to air dry.

In one embodiment multiple drops were placed in a row and in another embodiment a row of spots containing 1, 2, 3 or 4 drops on the same spot was created to allow a gradient strip to measure the capacity of the treated towel to absorb odor. The coating on the towel absorbs the odor and the visual indicating agent, being sensitive to the odor, reacts with the odor and slowly changes color.

The towel was attached inside the top of the container and was prevented from coming into contact with the solution of isovaleric acid. Within 3 minutes the color of the first spot had changed from red to almost yellow, indicating the presence and absorption of acid odor. With time the other spots changed from red to yellow, reflecting the dye concentration in the spot, i.e. the higher the dye concentration the longer the time taken to change color.

By following the same procedure cresol red, neutral red, 3-nitrophenol, Brilliant Yellow, bromothymol blue and chlorophenol red (all available from Aldrich Chemical) were also shown to be sensitive to low concentrations (0.01 to 0.0015% wt/wt) of aliphatic acid adors, with a color change becoming visible within 3 to 30 minutes of exposure to the acid odor, the time depending on the concentration of the indicating agent applied to the towels.

The color range was extended by mixing phenol red with a small amount of F,D&C Blue 1 dye (also available from Aldrich Chemical) to convert the initial color to orange/brown. On exposure of the spot to acid odor, the orange/brown color changed to green, indicating the absorption of the acid odor (the phenol red dye is converted to a yellow color by acid odors while the F,D&C Blue 1 dye is not sensitive to acid odors and therefore remains unchanged. The resulting spot is thus a mixture of yellow and blue, which results in a green spot). Thus, it was shown that it is possible to obtain a variety of color changes based on color mixing of primary colors.

EXAMPLE 2

In order to test the ability of Michler's Hydrol to detect thiols, 1 ml of a reaction mixture was placed into each of 6 vials containing 10 µl of furfuryl mercaptan (0, 0.228, 0.456, 0.912, 1.824 and 3.648 ppm, respectively), 980 µl of buffer containing 40 mM sodium acetate and 4 moles/liter guanidine chloride, pH 5.1 and 10 µl of 0.65 mg/ml MH dye (BDMB), all available from Aldrich Chemical Chemical Co. After incubation of all the vials at room temperature for less than 5 minutes, a portion (200 µl) from each vial was transferred to a microtiter plate well, and the absorbance at 590 nm was measured using a microtiter plate reader (Dynex Technologies of Chantilly, Va. (Model # MRX)). The absorbance can also be measured in the range of 580-615 nm.

As shown in FIG. 1, a standard curve was derived using furfuryl mercaptan as a model thiol odorous compound detectable by the BDMB method. In FIG. 1 the x-axis is the concentration of furfuryl mercaptan in ppm from 0 to 4 and the y-axis is the inverse of the absorbance at 590 nm. The sensitivity of thiol detection was found to be very high in this method, and it was even more sensitive than the gas chromatography headspace method described below.

EXAMPLE 3

As garlic has a sulfur compound (diallyl thiosulfinate (allicin)) as its major odorous component, this was used as a practical example to test the reaction of Michler's Hydrol to sulfur odors. Fresh-cut garlic was placed in a jar with a MH-dyed Scott® paper towel and the jar was sealed. The paper towel in the garlic containing jar was observed to change color (from blue to colorless) within 3-5 minutes, whereas no color change was observed in a control jar.

EXAMPLE 4

Figure 2:
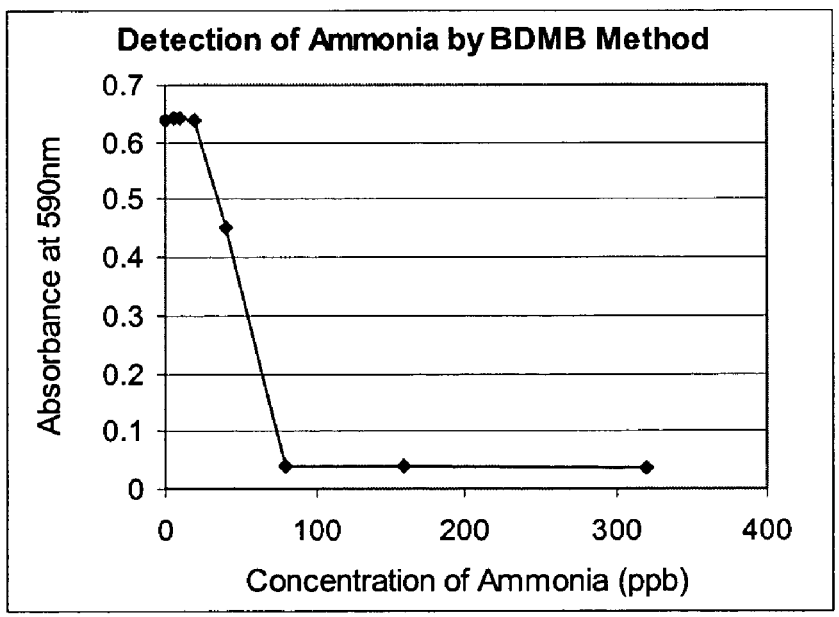
FIG. 2 shows a standard curve for the detection of ammonia by BDMB.

As shown in FIG. 2, a standard curve was derived using ammonium hydroxide solution as an ammonia odor source detected by BDMB (MH-dye). In FIG. 2 the x-axis is the concentration of ammonia in ppb from 0 to 400 and the y-axis is the absorbance at 590 nm. Into each of 8 vials, 50 µl of a specific concentration of ammonia solution (0, 0.01, 0.02, 0.04, 0.08, 0.16, 0.32, and 0.64%, respectively) was mixed with 150 µl of MH solution (20 µl of 10.0 mg/ml MH in $CH_3CN$ with 5.0 ml of 40 mM sodium acetate and 4 M guanidine HCl, pH 5.1), all available from Aldridge Chem. Co. of Milwaukee, Wis. and the vials were sealed and incubated for less than 4 min.

The solutions were then transferred to microtiter plate wells and the absorbances were measured at 590 nm using the microtiter plate reader from Dynex Technologies of Chantilly, Va. (Model # MRX). The absorbance readings were plotted against the concentrations of ammonia solutions, with the concentrations being represented as parts per billion (ppb). The sensitivity of ammonia detection was very high according to the MH-dye method, and it was shown that the sensitivity could be altered by varying the MH-dye concentration.

EXAMPLE 5

Figure 3:
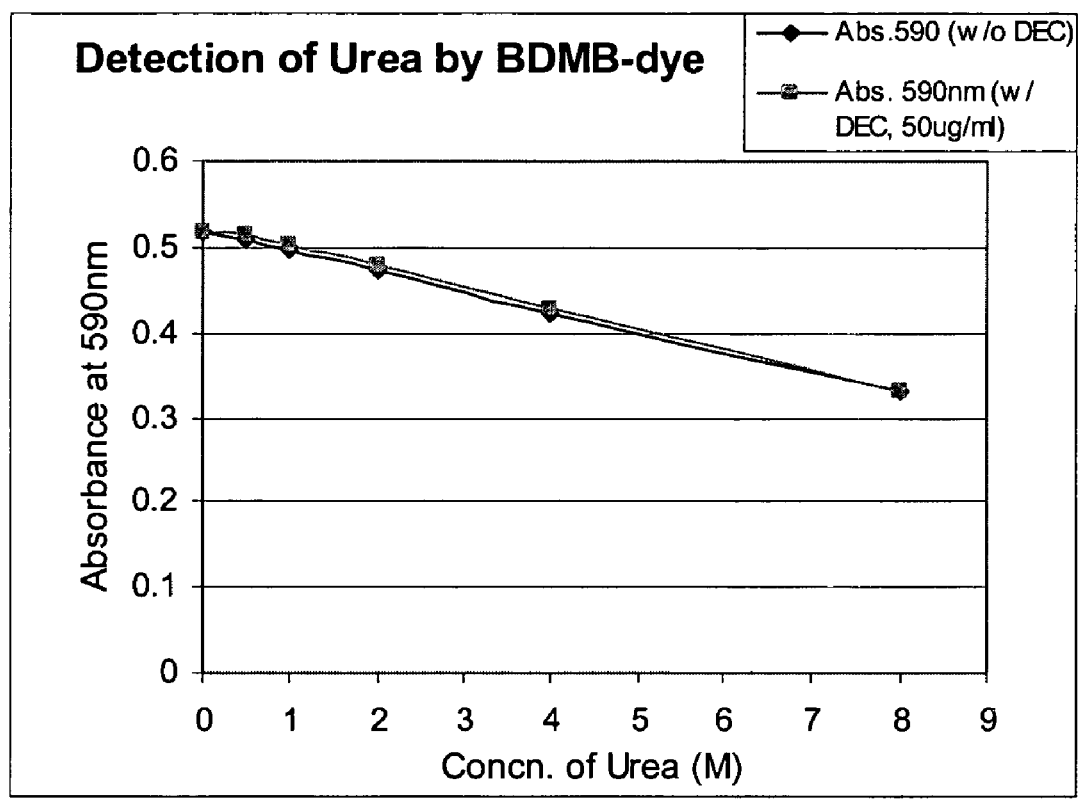
FIG. 3 shows a standard curve for the detection of urea by BDMB.

A standard curve was also prepared for the detection of urea odors by BDMB (FIG. 3) using the same methodology as described above, and BDMB was also found to be sensitive for this odor. In FIG. 3 the x-axis is the concentration of urea in moles per liter from 0 to 9 and the y-axis is the absorbance at 590 nm.

EXAMPLE 6

Odor absorption was determined using headspace gas chromatography testing conducted on an Agilent 5890, Series II gas chromatograph with an Agilent 7694 headspace sampler, both available from Agilent Technologies, Waldbronn, Germany. Helium was used as the carrier gas (injection port pressure: 12.7 psig (188.9 kPa); headspace vial pressure: 15.8 psig (210.3 kPa); supply line pressure: 60 psig (515.1 kPa)). A DB-624 column that had a length of 30 m and an internal diameter of 0.25 mm was used for the odorous compound (available from J&W Scientific, Inc. of Folsom, Calif.).

The operating parameters used for the headspace gas chromatography are shown below in Table 4.

TABLE 4

Operating Parameters for the Headspace Gas Chromatography Device
Headspace Parameters

| Zone Temps, ° C. | Oven | 37 |
| --- | --- | --- |
| | Loop | 42 |
| | TR. Line | 47 |
| Event Time, minutes | GC Cycle time | 10.0 |
| | Vial eq. Time | 10.0 |
| | Pressuriz. Time | 0.20 |
| | Loop fill time | 0.20 |
| | Loop eq. Time | 0.15 |
| | Inject time | 0.30 |
| Vial Parameters | First vial | 1 |
| | Last vial | 1 |
| | Shake | [off] |

The test procedure involved placing 0.005-0.006 g of a sample containing the odor absorbing agent in a 20 cubic centimeter (cc) headspace vial. Using a syringe, an aliquot of the odorous compound was also placed in the vial. The vial was then sealed with a cap and a septum and placed in a headspace gas chromatography oven at 37° C. After ten minutes, a hollow needle was inserted through the septum and into the vial. A 1 cc sample of the headspace (air inside the vial) was then injected into the gas chromatograph.

Initially, a control vial with only the aliquot of odorous compound was tested to define 0% odorous compound adsorption. To calculate the amount of headspace odorous compound removed by the sample, the peak area for the odorous compound from the vial with the sample was compared to the peak area from the odorous compound control vial. Testing was done with 5 µl of 2,3-butanedione, 5 µl of acetaldehyde, and 5 µl of 3-methyl butanal. Each sample was tested in duplicate.

EXAMPLE 7

The ability of BDMB to control or absorb sulfur (thiol) odors was determined using ethyl mercaptan (EtSH) from Aldrich Chemical as a specific example of a sulfur odor.

A control sample containing 1 ml of the above buffer and water was prepared in a closed vial. A sample containing only 1 ml of buffer was also prepared, as were two samples containing 1 ml of 0.5 mg/ml and 2.0 mg/ml MH, respectively. A sample containing 1 ml of 0.5 mg/ml MH and 5 mM $ZnCl_2$, both from Aldrich Chemical, was also prepared to ascertain the effect of the addition of a metal salt to the MH, and then a final sample containing 5 mM $ZnCl_2$ only was prepared.

2.0 mg of ethyl mercaptan was injected into each sample and the samples were left to stand at room temperature for about 5 minutes. 1 ml of headspace from each sample was then determined by GC analysis according to the method described above, and the results are shown in Table 5.

TABLE 5

Absorption of ethyl mercaptan (EtSH) by MH in the presence and absence of metal salts

| Sample | Volume of head space from 2 mg EtSH (ml) | Area of the Peak in GC Analysis (AU) | % Odor Reduction |
| --- | --- | --- | --- |
| Control | 1.0 | 1 061 270 | — |
| Buffer alone | 1.0 | 867 528 | 18.3 |
| MH (0.5 mg/ml) | 1.0 | 712 649 | 32.9 |
| MH (2.0 mg/ml) | 1.0 | 667 661 | 37.1 |
| MH (0.5 mg/ml) + $ZnCl_2$ (5 mM) | 1.0 | 638 016 | 39.9 |
| $ZnCl_2$ (5 mM) alone | 1.0 | 8709 78 | 17.9 |

From these results, it is apparent that BDMD is suitable for both absorbing and indicating the presence of a sulfur odor. Furthermore, the results show that the rate of absorption of odorous compounds by BDMB is enhanced when a metal salt is added.

EXAMPLE 8

The effect of BDMB on the absorption of urine odors was also determined by comparing the effect of adding BDMB to a sample containing urine with a sample to which no BDMB had been added (Table 6).

A first control sample (control 1) containing 2 ml of urine was prepared in a closed vial, and a second control sample (control 2) containing 2 ml of urine placed on a pad was also placed in a closed vial. Vials containing 1 mg urease and 0.15 mg MH, respectively (all available from Aldrich Chemical), were prepared, and a pad with 2 ml urine (as per control 2) was placed into each of these vials.

The samples were left to stand at room temperature for about 5 minutes. 1 ml of headspace from each sample was then determined by GC analysis according to the method described above.

The results indicate that BDMB is effective to reduce the peak (RT 0.77 min) obtained in the GC headspace analysis of urine. Additionally, it was also observed, based on a sniff-test, that BDMB-treated urine has no significant odor.

TABLE 6

Effect of urease and MH on the GC peaks obtained from the headspace of urine samples

| # | System | Area of the peak at RT 0.77 min | % Change of the peak at RT 0.77 min | Area of the Peak at RT 1.95 min ($\times 10^6$) |
|---|--------|----|----|----|
| 1 | Only Urine (2 ml) (Control1) | 434015 | — | 1.228 |
| 2 | Urine (2 ml) + pad (0.3 g) (Control 2) | 705262 | — | 1.126 |
| 3 | Control 2 with urease (1 mg) | 917030 | +30.0 | 1.162 |
| 4 | Control 2 with MH (0.15 mg) | 299491 | −57.5 | 1.227 |

EXAMPLE 9

To confirm that BDMB is suitable for use as an indicating agent for sulfur odors, four KIMWIPES® tissues, available from Kimberly-Clark Corporation, Dallas, Tex., USA, were dyed with MH (0.5 mg/ml) from Aldrich Chemical. $ZnCl_2$ (5 mM), also from Aldrich Chemical, was added to two of the KIMWIPES® tissues. Each KIMWIPES® tissue was placed in a closed vial, and ethyl mercaptan (EtSH) odor (also from Aldrich Chemical) was injected into one vial containing a KIMWIPES® tissue with MH only, and into one vial containing a KIMWIPES® tissue with both MH and $ZnCl_2$. In both instances, a marked change in color was observed between the vials containing the odor and the vials into which the odor was not injected (not shown).

It was therefore concluded that BDMB is an effective, multi-functional odor reducing agent for sulfur, amine and ammonia odors which are major components of, among others, urine, feces, dog and cooking odors.

EXAMPLE 10

SNOWTEX-C® silica nanoparticles from Nissan Chemical were modified by placing 20 mg copper chloride in 20 ml of a 20% wt/wt SNOWTEX-C® nanoparticle suspension. KIMWIPES® tissues from Kimberly-Clark Corporation were coated with the copper ion modified silica nanoparticle suspension and allowed to air dry. These light green colored KIMWIPES® tissues were placed into a vial and exposed to 10 ppm ethyl mercaptan odor (Aldrich Chemical). The KIMWIPES® tissues immediately turned blue giving a visual indicator of absorption of odor and that the odor absorbing tissue was working. The experiment was repeated with the copper chloride being in a dry powder form, and the same color change was observed.

EXAMPLE 11

A KIMWIPES® tissue was coated with a 1% wt/wt solution of Rose Bengal Dye (Acid Red 94) from Aldrich Chemical and air-dried. This bright red dye was rapidly decolorized when exposed to ethyl mercaptan, also from Aldrich Chemical. Both a water solution and a dried coating of the indicating agent turned colorless when exposed to ethyl mercaptan.

EXAMPLE 12

D&C Red 28 dye (Acid Red 92), a drug- and cosmetic use-approved dye, was identified as a suitable visual indicating agent and reduced to practice by decolorizing on exposure to sulfur odors. It was demonstrated to work both as a water solution and as a dry coating on a cellulose substrate (1% wt/wt water solution coated onto a SCOTT® paper towel and dried).

EXAMPLE 13

Cobalt chloride was found to be sensitive to sulfur, aldehyde and amine odors. It changed color from sky blue to colorless in the presence of an amine odor, to brown in the presence of sulfur odors and to green in the presence of aldehyde odors. Cobalt chloride was demonstrated to function both as a water solution and as a dry coating on a cellulose sheet (1% wt/wt water solution coated onto a SCOTT® paper towel).

EXAMPLE 14

The blue-colored copper phenanthroline complexes turned brown/orange on exposure to sulfur odors and green on exposure to amine odors. This was demonstrated both as water solutions and dry coatings on cellulose substrates (1% wt/wt water solution coated onto a Scott® paper towel).

EXAMPLE 15

Iron (III) chloride, a yellow/brown solid turned colorless or brown/black when exposed to sulfur or amine odors in a dry powder state. It can be a coating on a substrate (1% w/wt water solution coated onto a Scott® paper towel) or a coating on a silica or alumina powder (Nissan Chemical).

EXAMPLE 16

In addition to coating the visual indicating agent onto a substrate as described in the previous examples, it was also demonstrated that a solution of the indicating agent can also be printed onto the substrate using an inkjet printer. Inkjet printing deposits a thin coating of indicating agent on top of the substrate, potentially allowing a more sensitive color coating on the substrate.

Michler's Hydrol from Aldrich Chemical was formulated with inkjet additives shown in Table 7.

TABLE 7

Inkjet formulation containing a visual indicating agent (MH)

| INK COMPONENT | VOLUME (ml) |
|---|---|
| Water (deionized) | 0.85 |
| Ethylene glycol | 3.0 |
| Glycerol | 1.5 |
| Polyethylene glycol (200 MW) | 3.0 |
| 1,3-Propanediol | 1.5 |
| Michler's Hydrol (1.5 mg/ml) in 40 mM sodium acetate and 4 M guanidine HCl, pH 5.1 | 40.1 |
| TOTAL | 50 |

The ink solution was loaded into empty Margarita® cartridges (Part #0900400-300) obtained from McDermid-Colorspan of Eden Prairie, Minn. and printed using a wide format McDermid-Colorspan printer (Model XII). Good inkjet printing on Scott® paper towel substrate was demonstrated. A strip of the printed Scott® paper towel was then exposed to garlic odor and the blue color was observed to decolorize in 10 seconds (compared to 3-5 minutes taken to observe the color change of a Scott T® paper towel saturated with MH according to one of the previous examples). Higher sensitivity to the odor was thus observed by inkjet printing the indicating agent onto the substrate.

EXAMPLE 17

Figure 4:
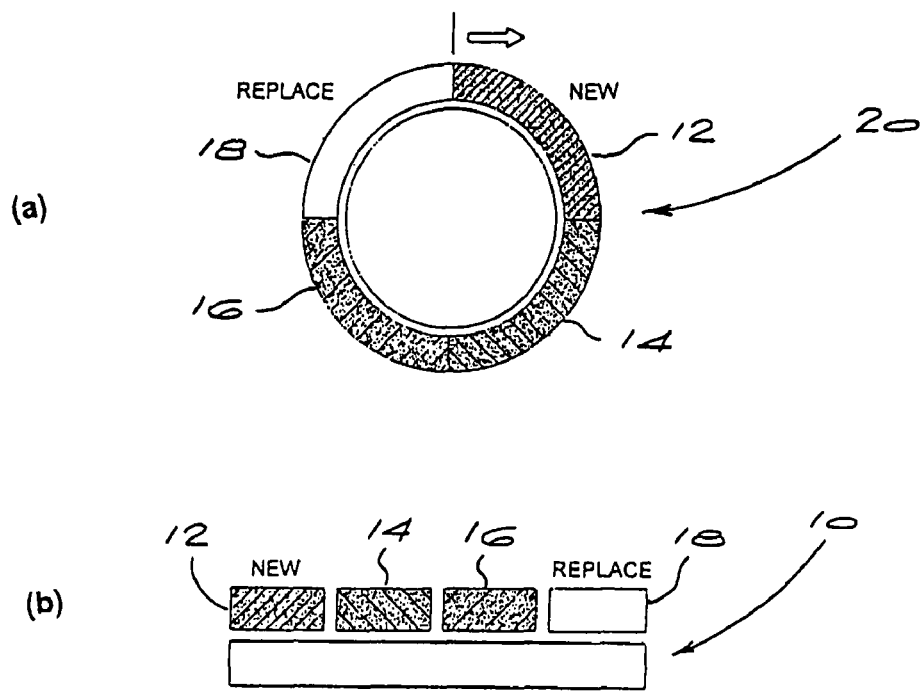
FIGS. 4(a) and 4(b) show two possible designs for a strip or patch forming the indicator device of the invention.

FIGS. 4(a) and 4(b) show two possible designs for a strip 10 or patch 20 forming the indicator device of the invention, but it will be apparent to any person who is skilled in the art that any other type of design could be used, for example, a floral design, text, a series of dots, and so forth. The patch 20 and strip 10 of FIGS. 4(a) and (b), respectively, are divided into four zones 12, 14, 16 and 18 (by way of example only), with the first zone 12 marked "New" containing the lowest concentration of indicating agent and the fourth zone 18 marked "Replace" containing the highest concentration of indicating agent.

By measuring the odor absorption capacity of the sheet or article (mg odor absorbable/gram of sheet) and knowing that the indicating agent reacts with the odor compound (mole of odor compound/mole of indicating agent), the odor absorption capacities can be matched to tune the indicating agent to the odor absorption of the sheet or article.

Thus, if none of the zones have changed color, this indicates that the product has been exposed to less than 25% of its odor absorbing capacity. As the product is exposed to odor, so the zones will begin to change color, with the first zone 12 changing color when 25% of the odor absorbing capacity of the article to which it is attached has been reached, the second zone 14 changing color after 50% of the odor absorbing capacity has been reached, and so on, until the fourth and end zone 18 will change color when 100% of the odor absorbing capacity has been reached.

Figure 5:
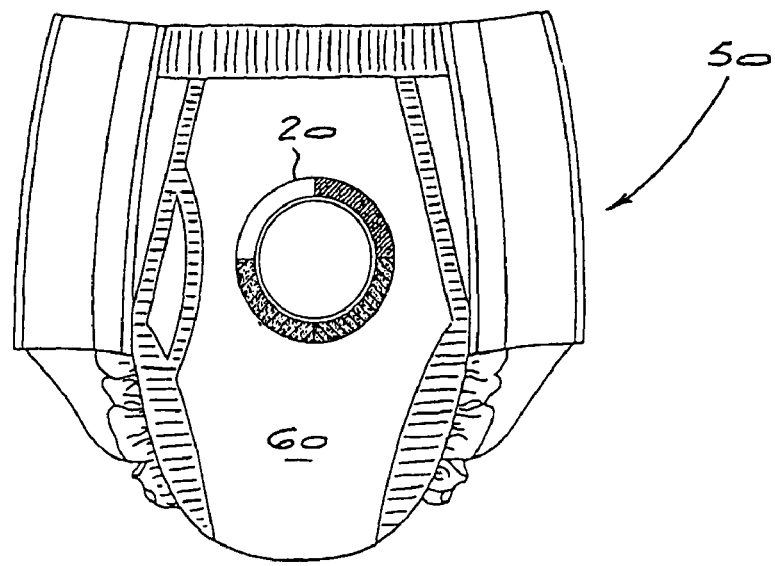
FIG. 5 shows a disposable diaper with an indicating device according to one embodiment of the invention.

FIG. 5 shows a disposable diaper 50 having an outer cover 60 onto which a visual indicating patch 20, as described above, has been printed.

While the invention has been described in detail with respect to specific embodiments thereof, it will be apparent to those skilled in the art that various alterations, modifications and other changes may be made to the invention without departing from the spirit and scope of the present invention. It is therefore intended that the claims cover or encompass all such modifications, alterations and/or changes.

What is claimed is:

1. An article for controlling odor, the article comprising a substrate which includes an odor absorbing agent and at least one visual indicating agent in an amount effective to change color when exposed to an odor, the odor absorbing agent comprising nanoparticles, the visual indicating agent being present in differing concentrations in two or more juxtaposed zones on the substrate, the concentrations in the two or more juxtaposed zones configured to indicate to the user the odor absorbing capacity remaining in the article such that the zone with the lowest concentration of visual indicating agent changes color first and the zone with the highest concentration of visual indicating agent changes color last so that the remaining odor absorbing capacity can be determined based on the number of zones which have yet to undergo the color change, wherein the at least one visual indicating agent is selected from the group consisting of 4,4'-bis(dimethylamino)-benzhydrol, pararosaniline, alpha-naphtholbenzene, and naphthochrome green.

2. The article of claim 1, wherein the indicating agent indicates when the article has been exposed to sufficient odor to saturate the article by changing color.

3. The article of claim 1, wherein the substrate is a disc, patch, strip, or combination thereof.

4. The article of claim 1, wherein the indicating agent is printed in solution onto the substrate and allowed to dry so that the dried residue of the solution remains on the substrate.

5. The article of claim 1, wherein the indicating agent is coated in solution onto the substrate and allowed to dry so that the dried residue of the solution remains on the substrate.

6. The article of claim 1, wherein the indicating agent is applied in differing concentrations in two or more juxtaposed zones to indicate how much of the odor absorbing capacity of the article has not been utilized.

7. The article of claim 1, wherein the indicating agent is applied in differing concentrations in two or more juxtaposed zones to indicate how much of the odor absorbing capacity of the article has been utilized.

8. The article of claim 1, wherein the odor is selected from the group consisting of body odor, foot odor, urinary odor, tobacco odor, meat odor, garbage odor, basement odor, and odors prevalent in other odorous elements and compounds, the odorous elements and compounds selected from the group consisting of mercaptans, sulfide, hydrogen sulfide, amines, ammonia, sulfur, sulfur degradation products, aliphatic acids, isovaleric acid, butyric acid and acetic acid.

9. The article of claim 1, wherein the visual indicating agent is 4,4'-bis(dimethylamino)-benzhydrol.

10. The article of claim 1, which is selected from a disposable odor absorbing sheet, diaper, undergarment pad, face mask, filtration device, sanitary napkin, tampon, panty shield and incontinence pad.

11. The article of claim 1, wherein the nanoparticles include silica, alumina, or combinations thereof.

12. The article of claim 1, wherein the substrate comprises fibers.

13. The article of claim 1, wherein the visual indicating agent is pararosaniline base.

14. The article of claim 1, wherein the visual indicating agent is present in an amount of from about 0.001 to 15 wt. %.

15. The article of claim 1, wherein the visual indicating agent is present in an amount of from about 1.1 to 1 wt. %.

16. The article of claim 1, wherein the visual indicating agent is alpha-naphtholbenzene.

17. The article of claim 1, wherein the visual indicating agent is naphthochrome green.

18. The article of claim 1, wherein the nanoparticles are modified with a metal ion, a chlorite ion, a persulfate ion, a permanganate ion, or combinations thereof.

19. The article of claim 18, wherein the metal ion is selected from the group consisting of copper ion, silver ion, gold ion, iron ion, and combinations thereof.

20. The article of claim 1, wherein the odor absorbing agent further comprises activated charcoal, sodium bicarbonate, clay, zeolites, molecular sieves, or combinations thereof.

21. A method for visually indicating when an article for controlling odor is saturated comprising the steps of:
introducing into or onto the article an odor absorbing agent, the odor absorbing agent comprising nanoparticles;
introducing into or onto the article a visual indicating agent that is color sensitive to the odor, wherein the visual indicating agent is introduced in different concentrations in two or more juxtaposed zones into or onto the article, the visual indicating agent configured to provide a change in color that is indicative of the odor absorbing capacity remaining in the article such that the zone with the lowest concentration of visual indicating agent changes color first and the zone with the highest concentration of visual indicating agent changes color last so that the remaining odor absorbing capacity can be determined based on the number of zones which have yet to undergo the color change, wherein the visual indicating agent is selected from the group consisting of 4,4'-bis (dimethylamino)-benzhydrol, pararosaniline, alpha-naphtholbenzene, and naphthochrome green, and observing the change in color of the visual indicating agent when the article is saturated with the odor.

22. The method of claim 21, wherein the visual indicating agent is 4,4'-bis(dimethylamino)-benzhydrol.

23. The method of claim 21, wherein the visual indicating agent is pararosaniline base.

24. The method of claim 21, wherein the article is selected from a disposable odor absorbing sheet, diaper, undergarment pad, face mask, filtration device, sanitary napkin, tampon, panty shield and incontinence pad.

25. The method of claim 21, wherein the article comprises a substrate on which the visual indicating agent is disposed.

26. The method of claim 21, wherein the visual indicating agent is alpha-naphtholbenzene.

27. The method of claim 21, wherein the visual indicating agent is naphthochrome green.

28. The method of claim 21, wherein the nanoparticles include silica, alumina, or combinations thereof.

29. The method of claim 21, wherein the nanoparticles are modified with a metal ion, a chlorite ion, a persulfate ion, a permanganate ion, or combinations thereof.

30. The method of claim 29, wherein the metal ion is selected from the group consisting of copper ion, silver ion, gold ion, iron ion, and combinations thereof.

31. The method of claim 21, wherein the odor absorbing agent further comprises activated charcoal, sodium bicarbonate, clay, zeolites, molecular sieves, or combinations thereof.

32. The method of claim 21, wherein at least one of the juxtaposed zones including the visual indicating agent is configured to change from a first color to a second color, the second color signifying that the article is saturated with odor.

33. The method of claim 21, wherein at least one of the juxtaposed zones including the visual indicating agent is configured to change from a first color to colorless, the lack of color signifying that the article is saturated with odor.

34. The method of claim 21, wherein at least one of the juxtaposed zones including the visual indicating agent is configured to change from colorless to a first color, the first color signifying that the article is saturated with odor.

* * * * *

UNITED STATES PATENT AND TRADEMARK OFFICE
CERTIFICATE OF CORRECTION

| | | |
|---|---|---|
| PATENT NO. | : 7,837,663 B2 | |
| APPLICATION NO. | : 10/687269 | |
| DATED | : November 23, 2010 | |
| INVENTOR(S) | : John Gavin MacDonald et al. | |

It is certified that error appears in the above-identified patent and that said Letters Patent is hereby corrected as shown below:

Column 16, Line 39 (Claim 15) "...of from about 1.1 to 1 wt.%." should read --...of from about 0.1 to 1 wt. % --

Signed and Sealed this
Fourth Day of October, 2011

David J. Kappos
*Director of the United States Patent and Trademark Office*